United States Patent
Elsalanty et al.

(10) Patent No.: US 7,182,785 B2
(45) Date of Patent: Feb. 27, 2007

(54) MANDIBULAR BONE TRANSPORT RECONSTRUCTION PLATE

(75) Inventors: Mohammed E. Elsalanty, Richardson, TX (US); Timothy D. Mulone, Dallas, TX (US)

(73) Assignee: Craniotech ACR Devices, LLC, Dallas, TX (US)

( * ) Notice: Subject to any disclaimer, the term of this patent is extended or adjusted under 35 U.S.C. 154(b) by 1 day.

(21) Appl. No.: 10/970,108

(22) Filed: Oct. 21, 2004

(65) Prior Publication Data

US 2005/0203628 A1   Sep. 15, 2005

Related U.S. Application Data

(60) Provisional application No. 60/552,272, filed on Mar. 11, 2004.

(51) Int. Cl.
*A61F 2/28* (2006.01)
(52) U.S. Cl. ...................... 623/17.17; 606/69
(58) Field of Classification Search ....... 623/17.17–19; 600/201, 235, 237–238; 606/53, 57, 60, 606/71, 105
See application file for complete search history.

(56) References Cited

U.S. PATENT DOCUMENTS

| | | | | |
|---|---|---|---|---|
| 5,364,396 A | * | 11/1994 | Robinson et al. | 606/53 |
| 6,053,919 A | * | 4/2000 | Talos et al. | 606/71 |
| 6,277,124 B1 | * | 8/2001 | Haag | 606/105 |
| 6,355,036 B1 | * | 3/2002 | Nakajima | 606/57 |
| 6,918,910 B2 | * | 7/2005 | Smith et al. | 606/60 |

FOREIGN PATENT DOCUMENTS

WO   WO 01/21082 A1   3/2001

OTHER PUBLICATIONS

Klein et al., "Initial experiences using a new implant based distraction system for alveolar ridge augmentation" *Int J Oral Maxillofac Surg* 30(2):167-9 (2001).
Genecov et al., Distraction Osteogenesis: The Clinical Experience at the International Craniofacial Institute—Dallas, Texas, *Distraction Osteogenesis Interactive Course on CD ROM*. GlobalMed Net 1:236-254 (1999) *available at* http://www.globalmednet.com/do-cdrom/Clinical/MandLeng/Genecov/gen001.htm.
Hidding et al., "Intraoral Vertical Bone Distraction of the Alveolar Ridge" *Distraction Osteogenesis Interactive Course on CD ROM*, GlobalMed Net 1999. *available at* http://www.globalmednet.com/docdrom/Clinical/Alveolar/Hidding/hd001.htm.
Guerrero and Bell, Intraoral Mandibular Bone Transport Using the DynaForm™ Distraction Device: A Case Report, *Distraction Osteogenesis Interactive Course on CD ROM*, GlobalMed Net (1999) *available at* http://www.globalmednet.com/do-cdrom/Clinical/Transp/guerrero/gr001.htm.

(Continued)

*Primary Examiner*—Eduardo C. Robert
*Assistant Examiner*—Annette R. Reimers
(74) *Attorney, Agent, or Firm*—Baker Botts L.L.P.

(57) ABSTRACT

This device can be used to create new bone to fill a gap in the mandible after surgical excision. It uses a bone reconstruction plate as a distraction device. The reconstruction plate fixes the bone stumps on both sides of the bone gap. In the middle segment of the plate overlying the bone gap, the transport bone disc is carried on a transport unit that moves along a rail on the outer surface of the reconstruction plate.

23 Claims, 2 Drawing Sheets

OTHER PUBLICATIONS

Herford "Use of a Plate-Guided Distraction Device for Transport Distraction Osteogenesis of the Mandible" *J Oral Maxillofac Surg* 62(4):412-20 (Apr. 2004).

Brochure, "The Thread-Lock™ Transport Distractor," KLS Martin L.P., manufactured by Medical Modeling LLC, 4 pages, undated.

Rubio-Bueno, P., et al., "Scientific Foundations, Experimental Mandibular Regeneration by Distraction Osteogenesis with Submerged Devices: Preliminary Results of a Canine Model," The Journal of Craniofacial Surgery, vol. 13, No. 2, 7 pages, Mar. 2002.

Ayoub, A.F., et al., "Segmental mandibular reconstruction by microincremental automatic distraction osteogenesis: an animal study," British Journal of Oral and Maxillofacial Surgery (2001) 39, 356-364, Accepted Apr. 19, 2001, Published online Jul. 5, 2001.

Kuriakose, M.A., et al., "Reconstruction of Segmental Mandibular Defects by Distraction Osteogenesis for Mandibular Reconstruction," Head & Neck, 9 pages, Oct. 2003.

Li, J., et al., "Reconstruction of mandibular symphyseal defects by trifocal distraction osteogenesis: an experimental study in Rhesus," International Journal of Oral & Maxillofacial Surgery, 0901-5027/020159 + 06, 6 pages, 2006 © 2005.

Müller, M.-C., et al., "A comparison of two types of free bone grafts as transport discs in segmental distraction for reconstruction of calvarial bone defects: an experimental study," Arch Orthop Trauma Surg (2004) 124, DOI 10.1007/s00402-004-0749-3, 665-674, Rec'd Jul. 15, 2003 Published online Oct. 28, 2004.

\* cited by examiner

MANDIBULAR BONE TRANSPORT RECONSTRUCTION PLATE

PRIORITY

This application claims the benefit of U.S. provisional application No. 60/552,272 file Mar. 11, 2004.

FIELD OF THE INVENTION

This device can be used to create new bone to fill a gap in the mandible after surgical excision. It uses a bone reconstruction plate as a distraction device. The reconstruction plate fixes the bone stumps on both sides of the bone gap. In the middle segment of the plate overlying the bone gap, the transport bone disc is carried on a transport unit that moves along a rail on the outer surface of the reconstruction plate.

BACKGROUND OF THE INVENTION

Segmental resection is a basic component of the surgical treatment of malignant mandibular tumors. Incidence of oral cancer in the US is 7.7/100,000 (30,000 case/year). Surgical resection may be followed by radiotherapy or chemotherapy. Definitive treatment of many of the more common benign tumors may also require segmental resection due to high incidence of local recurrence after simple curettage or intra-lesional excision. These tumors include ameloblastoma, myxoma, giant cell granuloma and recurrent keratocyst. Blast injuries and high impact trauma to the mandible may lead to segmental bone loss either directly or due to surgical debridement. Segmental bone loss may also result from repeated surgical debridement for treatment of chronic osteomyelitis of the mandible.

All these conditions require reconstruction of the lower jaw, including the bone, the gingiva and the teeth. After resection of malignant tumors, more soft tissue reconstruction is often necessary. This may include the floor of the mouth, the tongue, the cheek, the chin, in addition to adequate soft tissue covering of the major vessels of the neck following neck dissection. This has always been a challenging task. In spite of the wide variety of reconstruction methods, none of them is completely satisfactory.

The general aim of oral reconstruction is to restore both the normal physiology and the facial aesthetics. Physiological functions include the maxillo-mandibular occlusion, mastication (jaw dynamics), deglutition, mandibular continuity, sensibility of the mucosa, sufficient alveolar ridge height and thickness, lip competence and speech. Aesthetic goals include the general appearance of the reconstructed soft-tissue, facial symmetry, restoration of dentition, and preservation of the lower facial dimensions.

The principle current reconstruction methods include mandibular reconstruction plate with or without bone grafting. A traditional mandibular reconstruction plate is a rigid titanium bone plate that connects the remaining bone stumps after segmental excision. The maxillo-mandibular central occlusion has to be achieved first by intermaxillary wire fixation. The plate prevents displacement of bone segments, soft-tissue collapse, and preserves facial symmetry. Soft-tissue reconstruction is then carried out to provide the proper covering and lining of the plate. This is usually the first of two reconstruction steps. The second step, definitive bone reconstruction, is often delayed to allow for radiotherapy to take place, eliminate the possibility for local recurrence or simply not to add to the longevity of the first operation. However, some surgeons prefer to do primary bone reconstruction at the same setting provided that no radiotherapy is needed and no recurrence is anticipated. Others, however, prefer not to do the definitive bony reconstruction at all. Although good aesthetic results were reported with reconstruction plate alone with no bone replacement, this deprives the patient of having any restoration of occlusion, not even a removable lower denture.

During the second stage of reconstruction, the gap is explored, and the whole width of the tumor bed as well as the edges of the remaining bone is dissected. This step is often technically difficult due to extensive fibrosis, loss of anatomical planes and landmarks, and the possibility of vascular injury that can result in serious bleeding or injury to the oral mucosa. Communication with the oral cavity due to mucosal breaks during dissection has a high chance of resistant postoperative infection. After complete dissection, the plate is removed and the bone graft (either vascularized or non-vascularized) is inserted in its place. The procedure is lengthy and highly demanding especially when microvascular techniques are used. The overall outcome of this technique, with either primary or secondary bone reconstruction was less than satisfactory. Failure rate of metal plate with bone graft was between 16–29%, while complication rate varied from 45–81%. Some factors were found to be more related to graft failure, the most important of which are the amount of intra-operative blood loss and the occurrence of recipient site complications (e.g. fistula and infection).

Disadvantages of free non-vascularized bone graft include graft resorption, high incidence of failure due to resistant infection, especially with primary reconstruction, insufficient amount of bone for large gaps and donor site morbidity. Except for iliac crest graft, the harvested bone mass was not sufficient either for osseointegrated implant insertion or carrying a removable lower denture. Disadvantages of free vascularized bone graft (free flaps) are discussed in the next section.

A substitute for the reconstruction plate has been a titanium mesh, which is shaped according to the gap after tumor excision, and then it is filled with bone graft either immediately or at a later stage. Although the mesh does have to be removed after reconstruction, it still requires the use of large amount of autogenous bone graft, and has a high failure rate mainly due to resistant infection necessitating removal of the prosthesis. Again, rehabilitation of jaw function was not achieved by this method. The tendency towards definitive reconstruction of bone as a part of the primary surgery is growing over the years. However, achieving acceptable results with primary reconstruction methods was never an easy task.

The use of non-vascularized bone graft during primary reconstruction is not advised due to high incidence of failure. The description of microvascular techniques in the early seventies provided more options for primary reconstruction of the mandible. Over the years, many designs for vascularized osseomyocutanous flaps for mandibular reconstruction were reported; the most popular of which are the vascularized fibula, scapula and iliac crest. They had better functional results, with the possibility to carry tooth restorations for full mouth rehabilitation, and the ability to reconstruct large and composite defects, even in growing patients.

In spite of their promising success rate, free vascularized flaps have high rates of complications, especially medical complications, which may be as severe as postoperative death. These highly demanding techniques, which require a specialized surgical team, definitely add to the longevity and complications of the primary surgery. In an average procedure of tumor resection with free fibular graft mandibular reconstruction, two surgical teams are operating simultaneously for more than 10 hours. Considering the general condition of the cancer patient, reconstructive surgery should be as brief and less invasive as possible.

Other disadvantages of vascularized tissue transfer include donor site morbidity. Leg pain, ankle instability have been reported with the vascularized fibula; herneas, hip pain, and anesthesia of the lateral thigh with vascularized iliac crest; and limitation of shoulder range of motion with vascularized scapula. Additionally, the characteristics of each flap design limited its use to only specific defects.

Distraction Osteogenesis in Mandibular Reconstruction

Distraction osteogenesis is a process of new bone formation between two bone segments, when they are gradually separated by incremental traction. This pattern of bone elongation allows the surrounding soft tissues to adjust to the new skeletal dimensions through the series of adaptive changes called distraction histiogenesis. Active histiogenesis has been shown to occur in various soft tissues including skeletal muscles, nerves, blood vessels, periodontal ligament, and gingiva. The result will be the synthesis of new bone with a cover of periostium and soft tissues (mucosa, muscles, etc.) as well as new vascular and nerve supply.

Using this technique, bone defects in long bones could be reconstructed without bone grafting, but by surgically separating a bone segment (transport disc) from one, or both edges of the remaining bone and gradually distracting this segment in the direction of the opposite bone edge. New bone will develop behind the distracted segment filling the gap until it reaches the docking site. Recent results of mandibular reconstruction using this principle were very promising. Newly formed bone proved to have normal architecture (inner cortex, outer cortex, and medulla), dimensions, and 80–100% of normal mechanical properties when examined after 8 weeks of consolidation.

Distraction devices designed for reconstruction of mandibular bone defects had two forms. The first is a uni-or-multidirectional distraction device mounted on, or combined with reconstruction plate. The second is an extra-oral titanium arch with movable units anchored to mandibular bone segments through steel pins.

Distraction Devices Mounted on or Combined with Reconstruction Plate

Each of these devices is composed of a distraction device, which is either mounted on (connected to) the plate, or totally separate from it. The distraction device can be uni-directional or multi-vector; extra-oral or intra-oral. However, in addition to the technical problems associated with device assembly and application, the distraction devices had a completely independent function to the reconstruction plate. While the reconstruction plate takes the curved shape of the original mandible, the distraction device carries the transport segment towards the docking site guided by the linear vector of the distraction device irrelevant to the course of the reconstruction plate. In other words, the fixative function of the reconstruction plate was separated from the new bone formation, even when the two device components were physically connected. In addition, the length range of the regenerate is limited by the length of the device, which makes it unable to reconstruct large mandibular defect especially those crossing the midline.

Extra-oral Bone Transport Devices

In our experience with this design, it proved to be simple, fast, with minimal interference with bone segments, wider range of distraction for angle-to-angle reconstruction. Yet, its disadvantages included poor control of the transport disc, pin-tract infection, pin extrusion, and retrusion of the newly formed bone in case of anterior reconstruction.

SUMMARY OF THE INVENTION

This device can be used to create new bone to fill a gap in the mandible after surgical excision. It uses a bone reconstruction plate as a distraction device. The reconstruction plate fixes the bone stumps on both sides of the bone gap. In the middle segment of the plate overlying the bone gap, the transport bone disc is carried on a transport unit that moves along a rail on the outer surface of the reconstruction plate.

In our mandibular bone transport reconstruction plate, the transport track is the shaft of the reconstruction plate itself and not a separate device mounted on it. In other words, the transport unit glides on the middle segment of the plate itself. Therefore, the plate functions both as a rigid mandibular reconstruction plate and a bone-transport distraction device. The transport unit moves along the serrated groove on the surface of the middle segment of the plate by direct activation of a screw within the unit case. The screw threads interact with the serrations on the groove when the screw is turned pushing the whole unit in one direction, either forwards or backwards, according to the direction of screw turning. The foremost thread on the activation screw is sharply cut so that, while rotating, it cuts its way through any tissue growth that may be covering the serrations on the plate surface groove. The transport unit has a sloping edge to act as a dissector through the soft tissues as the unit is moving. The transport unit can be disassembled and removed after the end of distraction, while the plate itself can be retained in place for as long as desired. The transport unit is attached to the transport disc by 1.7 mm screws arranged in an alternating fashion, so that appropriate stability can be provided by fewer screws.

DETAILED DESCRIPTION OF THE INVENTION

This device can be used to create new bone to fill a gap in the mandible after surgical excision. It uses the rigid bone reconstruction plate as distraction device. The reconstruction plate fixes the bone stumps on both sides of the bone gap by large (2.3–2.7 mm, bicortical titanium bone screws). In the middle segment of the plate overlying the bone gap, the transport bone disc is carried on a transport unit that moves along a rail on the outer surface of the reconstruction plate when a screw within the unit is activated.

Figure 1:
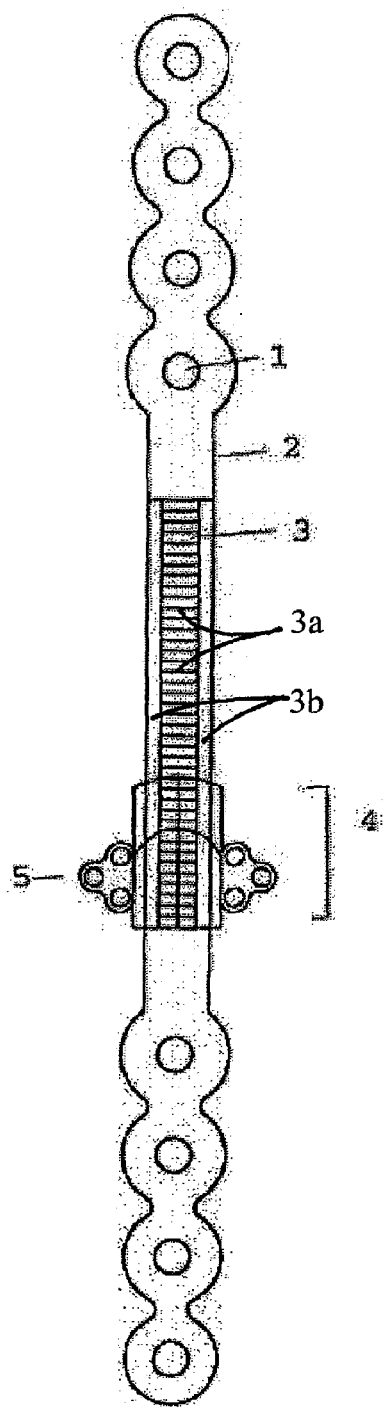
FIG. 1: Illustrates Mandibular Bone Transport Reconstruction Plate with the transport unit superimposed on the beginning of the rail.

The device is composed of a traditional titanium mandibular reconstruction plate (FIG. 1) with a middle segment (2) that functions as a straight track over which a transport unit can be moved from one end of the track to the other. The middle segment of the plate will be overlying the bone gap that resulted from surgical bone removal for any reason. The two ends of the plate (10 and 11) will be stabilized to the bone segments on both sides of the gap with 2.3–2.7 titanium screws. The transport unit will be stabilized to a bone disc cut out from one of the two bone segments to move it gradually (e.g. at a rate of 1 mm/day) until it reaches the other bone segment (See surgical procedure for details).

The outer surface of the middle segment has a serrated groove (3) comprising serrations (3a) so that the movable transport unit (4) can glide over it in one direction if a screw within it (6a and 6b) is turned clockwise, and glide back in the opposite direction when the gear is turned anti-clockwise. The middle segment comprises two substantially parallel guide rails (3b), with the serrations (3a) of the serrated groove (3) disposed between the guide rails (3b). Activation of the screw within the transport unit is carried out through an activation flex cable (not shown) that is fixed to the head of the activation screw (6a). Rotation of the flex cable causes the screw to rotate to the same degree. This rotation will cause the transport unit to move in the direction of bone transport for a calculated distance (e.g. one millimeter of linear movement for each 360 degree rotation of the activation rod). The screw can be oriented so that the head faces either forwards or backwards, reversing the movement of the transport unit in relation to the direction of rotation of the flex cable.

Figure 2:
FIG. 2: Illustrates a cross section in the intersegment of the plate (rail portion).
Figure 3:
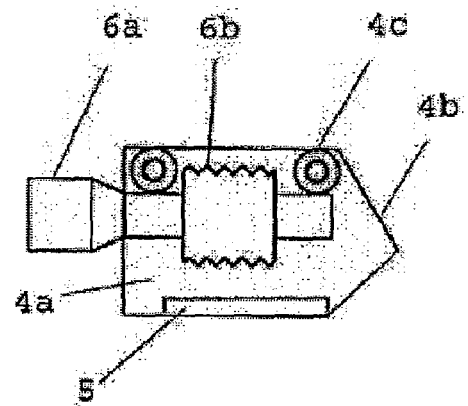
FIG. 3: Illustrates the transport unit with the activation screw.
Figure 4:
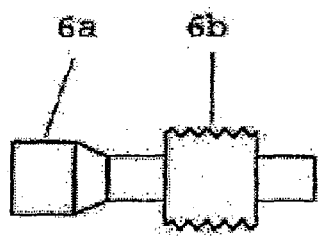
FIG. 4: Illustrates the composition of the activation screw.
Figure 5:
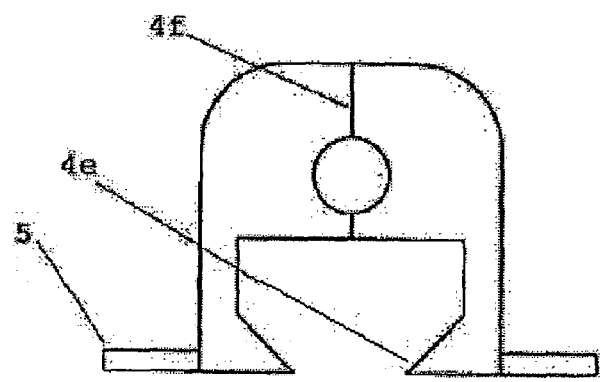
FIG. 5: Illustrates a cross section in the transport unit.

The inner surface of the middle segment of the plate has an undercut (FIG. 2) so that a countersink (4e), or a lip, in the transport unit (FIG. 5) fits into it for stabilization during the transport process. As soft tissues will be covering the device throughout the procedure, the leading edge of the movable transport unit is sloping (4b) to dissect through the tissues covering the plate and to minimize resistance to the movement of the transport unit beneath them. The thread of the screw (6b) is cut at its foremost end to be able to cut through any soft tissue growth that may be covering the serrations on the rail.

The transport unit is composed of two halves attached at the middle (4f) either by two connecting 1 mm screws (4c), or by interlocking snap segments (not shown). The plate is secured to the bony stumps on either sides of the bone gap by 3 to 4 titanium 2.3–2.7 mm screws (8) that are inserted bicortically, while the movable unit (4a) is secured to the transport bone segment (transport disc (7) through two, at least 3 hole-each, titanium miniplates (5) that hold 1.7 mm titanium miniscrews. The holes in the miniplates are arranged in an alternating fashion forming a small sheet with at least three holes on each side of the transport unit.

Surgical Procedure:

First, the maxillo-mandibular occlusion is maintained by intermaxillary wire fixation to maintain jaw relations. The appropriate length of the transport segment should be estimated before surgery and a number of plates with different lengths should be available during surgery to choose from. The device can be fixed to the mandibular bone stumps either before or after removal of the tumour segment by three bicortical screws on each side as in traditional reconstruction plate, leaving out approximately 2 cm of bone at the edge of one of the two bone segments, classically the posterior segment, so that it can be separated and fixed to the transport unit. After tumor resection, the transport unit is fixed to the potential transport block (transport disc) through the two miniplates (5) either before or after its separation. If immediate reconstruction is planned, a bicortical osteotomy to separate the transport segment is carried out during the same surgery. However, the surgeon may decide to delay the osteotomy according to the condition.

During the delay period, the device will function as a traditional reconstruction plate: stabilizing the bone segment, maintaining the maxillo-mandibular occlusion, preventing soft tissue collapse, and preserving the facial symmetry. Due to its intra-oral design, we expect the patient will tolerate it as comfortably as the traditional reconstruction plate. Reconstruction plates could be retained for years with minimal inconvenience to the patient.

Osteotomy is a procedure that takes around 15–30 minutes to complete. If delayed, it can be done under sedation and local anesthesia on an outpatient basis, as with the subsequent daily activation of the device. The buccal cortical plate is cut using an ultra thin micro saw and the osteotomy is then completed through the lingual cortex by a sharp osteotome. Care should be taken not to exert much force on the transport unit during bone separation. It may be helpful to take out the 3 screws of the upper plate in order to have some degree of mobility in the transport segment during separation. After complete separation of the segment, at least 4 secured mini-screws in total are preferred for the stability of the transport segment. The lingual mucosa should not be dissected at any time during the procedure to maintain the blood supply of the separated bone segment. The wound is then closed so that the activation cable protrudes through the mucosa into the oral cavity when the wound is closed. After 5–7 days of latency, activation of the device is started. Distraction rate is 0.5 mm/12 hours.

Figures 6A, 6B:
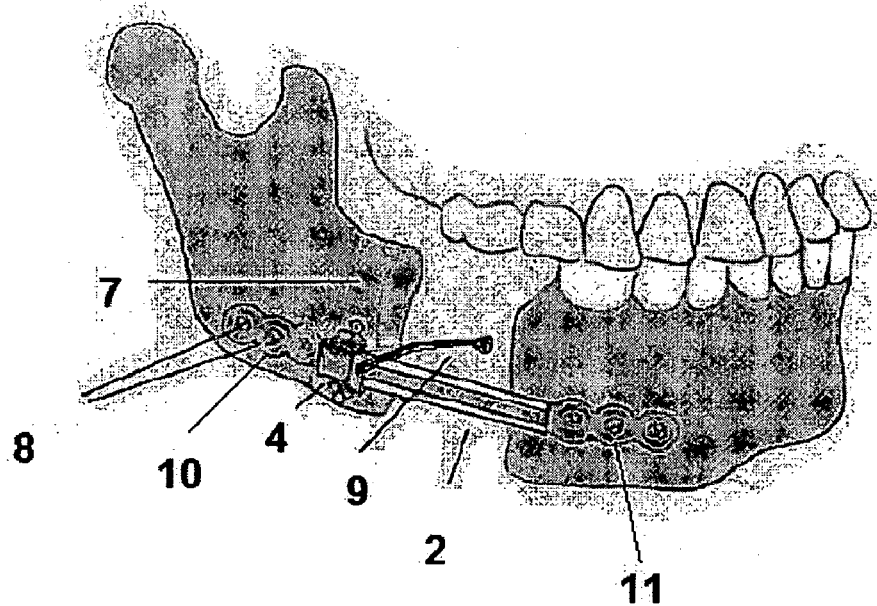
FIG. 6a: Illustrates the Mandibular Bone Transport Reconstruction Plate in place on the mandible before distraction is started.
FIG. 6b: Illustrates the Mandibular Bone Transport Reconstruction Plate in place while distraction is proceeding and new bone is being formed behind the transport disc.

Distraction is continued until the transport segment reaches the docking site. As the bone disc is transported, new bone is formed behind it to gradually fill the gap, according to the well-established principles of distraction osteogenesis. When the transport disc reaches the docking site (at the edge of the other bone segment), the device should be retained in place for a few weeks, depending on the amount of distraction, until the newly formed bone (12, FIG. 6B) consolidates and is able to sustain chewing forces or carry implants. Bone grafting may still be needed to promote bone union at the docking site. In this case, freshening of bone edges and the addition of small pieces of cancellous bone are usually sufficient.

The invention claimed is:

1. A mandibular bone transport device, comprising:
    a bone reconstruction plate comprising:
        a first end configured to couple the bone reconstruction plate to a first mandibular bone segment;
        a second end configured to couple the bone reconstruction plate to a second mandibular bone segment;
        a transport track disposed between the first and second ends and comprising serrations; and
    a transport unit distinct from the bone reconstruction plate, configured for coupling to a transport bone disc, and configured for advancing along the transport track of the bone reconstruction plate to advance the transport bone disc between the first and second mandibular bone segments, the transport unit comprising a threaded activation screw configured to interact with the serrations of the transport track to advance the transport unit along the transport track in response to rotation of the threaded activation screw; and a flexible cable coupled to the threaded activation screw of the transport unit such that rotation of the flexible cable rotates the threaded activation screw to advance the transport unit along the transport track of the bone reconstruction plate.

2. The device of claim 1, wherein the first and second ends of the bone reconstruction plate are connected to one another in a rigidly fixed configuration via the transport track.

3. The device of claim 1, wherein the bone reconstruction plate, including the first end, the second end, and the transport track, is integrally formed.

4. The device of claim 1, wherein the transport track of the bone reconstruction plate comprises two substantially parallel guide rails configured to guide the transport unit in advancing along the transport track.

5. The device of claim 1, wherein the transport unit comprises two halves configured to couple to each other such that the transport unit surrounds a portion of the transport track of the bone reconstruction plate.

6. The device of claim 1, wherein the transport unit comprises:
a first channel configured to surround a portion of the transport track of the bone reconstruction plate; and
a second channel configured to receive a threaded activation screw for advancing the transport unit along the transport track.

7. The device of claim 1, wherein the transport unit comprises a sloped leading edge to facilitate passage of the transport unit through tissue in advancing along the transport track of the bone reconstruction plate.

8. The device of claim 1, wherein the transport unit defines one or more openings configured to receive one or more screws to couple the transport unit to the transport bone disc.

9. The device of claim 1, wherein:
the first end of the bone reconstruction plate defines a plurality of openings configured to receive a plurality of screws to couple the first end of the bone reconstruction plate to the first mandibular bone segment, a first opening being located a first distance from the transport track and a second opening being located a second distance from the transport track, the second distance being at least twice the first distance; and
the second end of the bone reconstruction plate defines a plurality of openings configured to receive a plurality of screws to couple the second end of the bone reconstruction plate to the second mandibular bone segment, a first opening being located a first distance from the transport track and a second opening being located a second distance from the transport track, the second distance being at least twice the first distance;
such that the bone reconstruction plate is configured to rigidly fix the first mandibular bone segment to the second mandibular bone segment to prevent rotation and translation of the first and second mandibular bone segments relative to each other.

10. A method for mandibular distraction osteogenesis, comprising:
accessing a mandibular bone transport device comprising:
a bone reconstruction plate comprising:
a first end configured to couple the bone reconstruction plate to a first mandibular bone segment;
a second end configured to couple the bone reconstruction plate to a second mandibular bone segment; and
a transport track disposed between the first and second ends; and
a transport unit distinct from the bone reconstruction plate, configured for coupling to a transport bone disc, and configured for advancing along the transport track of the bone reconstruction plate to advance the transport bone disc between the first and second mandibular bone segments;
coupling the transport bone disc to the transport unit;
coupling the first end of the bone reconstruction plate to the first mandibular bone segment;
coupling the second end of the bone reconstruction plate to the second mandibular bone segment; and
advancing the transport unit along the transport track of the bone reconstruction plate to advance the transport bone disc between the first and second mandibular bone segments.

11. The method of claim 10, further comprising, while the first and second ends of the bone reconstruction plate are coupled to the first and second mandibular bone segments:
decoupling the transport unit from the transport bone disc; and
decoupling the transport unit from the transport track of the bone reconstruction plate.

12. The method of claim 10, wherein the first and second ends of the bone reconstruction plate are connected to one another in a rigidly fixed configuration via the transport track.

13. The method of claim 10, wherein the bone reconstruction plate, including the first end, the second end, and the transport track, is integrally formed.

14. The method of claim 10, wherein advancing the transport unit along the transport track of the bone reconstruction plate comprises rotating a threaded activation screw of the transport unit such that the threaded activation screw interacts with serrations of the transport track to advance the transport unit along the transport track.

15. The method of claim 14, wherein rotating the threaded activation screw of the transport unit comprises rotating a flexible cable coupled to the threaded activation screw to advance the transport unit along the transport track of the bone reconstruction plate.

16. The method of claim 10, wherein the transport track of the bone reconstruction plate comprises two substantially parallel guide rails that guide the transport unit in advancing along the transport track.

17. The method of claim 10, wherein the transport unit comprises two halves that couple to each other such that the transport unit surrounds a portion of the transport track of the bone reconstruction plate.

18. The method of claim 10, wherein the transport unit comprises:
a first channel that surrounds a portion of the transport track of the bone reconstruction plate; and
a second channel that receives a threaded activation screw for advancing the transport unit along the transport track of the bone reconstruction plate.

19. The method of claim 10, wherein the transport unit comprises a sloped leading edge that facilitates passage of the transport unit through tissue in advancing along the transport track of the bone reconstruction plate.

20. The method of claim 10, wherein the transport unit defines one or more openings that receive one or more screws to couple the transport unit to the transport bone disc.

21. The method of claim 10, wherein:

the first end of the bone reconstruction plate defines a plurality of openings that receive a plurality of screws to couple the first end of the bone reconstruction plate to the first mandibular bone segment, a first opening being located a first distance from the transport track and a second opening being located a second distance from the transport track, the second distance being at least twice the first distance; and the second end of the bone reconstruction plate defines a plurality of openings that receive a plurality of screws to couple the second end of the bone reconstruction plate to the second mandibular bone segment, a first opening being located a first distance from the transport track and a second opening being located a second distance from the transport track, the second distance being at least twice the first distance;

such that the bone reconstruction plate rigidly fixes the first mandibular bone segment to the second mandibular bone segment to prevent rotation and translation of the first and second mandibular bone segments relative to each other.

22. A mandibular bone transport device, comprising:

an integrally formed bone reconstruction plate comprising:
- a first end configured to couple the bone reconstruction plate to a first mandibular bone segment;
- a second end configured to couple the bone reconstruction plate to a second mandibular bone segment; and
- a transport track rigidly connecting the first end to the second end, comprising:
    - two substantially parallel guide rails; and
    - serrations disposed between the guide rails;

a transport unit distinct from the bone reconstruction plate, configured for coupling to a transport bone disc, and comprising:
- two halves configured to couple to each other such that the transport unit surrounds a portion of the transport track of the bone reconstruction plate; and
- a threaded activation screw configured to interact with the serrations of the transport track of the bone reconstruction plate to advance the transport unit along the guide rails of the transport track to advance the transport bone disc between the first and second bone segments in response to rotation of the threaded activation screw; and a flexible cable coupled to the threaded activation screw of the transport unit such that rotation of the flexible cable rotates the threaded activation screw to advance the transport unit along the transport track of the bone reconstruction plate.

23. The device of claim 22, wherein:

the first end of the bone reconstruction plate defines a plurality of openings configured to receive a plurality of screws to couple the first end of the bone reconstruction plate to the first mandibular bone segment, a first opening being located a first distance from the transport track and a second opening being located a second distance from the transport track, the second distance being at least twice the first distance; and the second end of the bone reconstruction plate defines a plurality of openings configured to receive a plurality of screws to couple the second end of the bone reconstruction plate to the second mandibular bone segment, a first opening being located a first distance from the transport track and a second opening being located a second distance from the transport track, the second distance being at least twice the first distance;

such that the bone reconstruction plate is configured to rigidly fix the first mandibular bone segment to the second mandibular bone segment to prevent rotation and translation of the first and second mandibular bone segments relative to each other.

* * * * *